(12) United States Patent
Watanabe et al.

(10) Patent No.: US 11,042,020 B2
(45) Date of Patent: Jun. 22, 2021

(54) ENDOSCOPE HAVING OBSERVATION WINDOW WITH CIRCUMFERENTIAL SIDE SURFACE AND CLEANING NOZZLES DIRECTED TO CIRCUMFERENTIAL SIDE SURFACE

(71) Applicant: OLYMPUS CORPORATION, Tokyo (JP)

(72) Inventors: Takanori Watanabe, Fuchu (JP); Hiromasa Okano, Ome (JP); Takashi Ito, Chofu (JP)

(73) Assignee: OLYMPUS CORPORATION, Tokyo (JP)

(*) Notice: Subject to any disclaimer, the term of this patent is extended or adjusted under 35 U.S.C. 154(b) by 416 days.

(21) Appl. No.: 16/035,916

(22) Filed: Jul. 16, 2018

(65) Prior Publication Data
US 2018/0325359 A1 Nov. 15, 2018

Related U.S. Application Data (63) Continuation of application No. PCT/JP2016/083058, filed on Nov. 8, 2016.

(30) Foreign Application Priority Data

Jan. 18, 2016 (JP) .............................. JP2016-006995

(51) Int. Cl.
*G02B 23/24* (2006.01)
*A61B 1/00* (2006.01)
*A61B 1/12* (2006.01)

(52) U.S. Cl.
CPC .......... *G02B 23/24* (2013.01); *A61B 1/00091* (2013.01); *A61B 1/00096* (2013.01); *A61B 1/126* (2013.01)

(58) Field of Classification Search
CPC .......................... A61B 2562/245; A61B 1/127
See application file for complete search history.

(56) References Cited

U.S. PATENT DOCUMENTS 9,214,364 B2   12/2015  Dobashi et al.
2011/0112363 A1  5/2011  Koga et al.
(Continued)

FOREIGN PATENT DOCUMENTS

CN      102728580 A    10/2012
JP      2002-238906 A   8/2002
(Continued)

OTHER PUBLICATIONS

International Search Report dated Dec. 13, 2016 issued in PCT/JP2016/083058.

*Primary Examiner* — Michael J Carey
*Assistant Examiner* — Minqiao Huang
(74) *Attorney, Agent, or Firm* — Scully, Scott, Murphy & Presser, P.C.

(57) ABSTRACT

An endoscope including an elongated insertion section; a side observation window that includes a tapered part on a side circumference intersecting in a longitudinal axis direction of the insertion section, a circumferential side surface formed in a cone shape; and a cleaning nozzle that includes an opening through which liquid cleaning the circumferential side surface of the side observation window is ejected. The opening is inclined to direct an ejection direction of the liquid toward a distal end of the tapered part. A center position of the opening part of the cleaning nozzle is provided on a proximal end side with respect to a center position of the side observation window in the longitudinal axis direction.

10 Claims, 8 Drawing Sheets

(56) References Cited

U.S. PATENT DOCUMENTS

| | | | | |
|---|---|---|---|---|
| 2011/0273549 A1* | 11/2011 | Kase | ............... | A61B 1/00177 |
| | | | | 348/68 |
| 2011/0282148 A1* | 11/2011 | Kase | ............... | A61B 1/00177 |
| | | | | 600/113 |
| 2011/0282155 A1* | 11/2011 | Kase | ................ | A61B 1/0615 |
| | | | | 600/165 |
| 2012/0226104 A1* | 9/2012 | Ikeda | ................... | A61B 1/07 |
| | | | | 600/129 |
| 2013/0070072 A1* | 3/2013 | Honda | ............ | A61B 1/00163 |
| | | | | 348/76 |
| 2013/0137923 A1* | 5/2013 | Honda | ............ | A61B 1/00096 |
| | | | | 600/109 |
| 2014/0346332 A1* | 11/2014 | Honda | ............... | G02B 23/243 |
| | | | | 250/227.21 |
| 2015/0073218 A1* | 3/2015 | Ito | ................... | A61B 1/00096 |
| | | | | 600/157 |
| 2016/0338575 A1* | 11/2016 | Honda | ............... | G06T 3/0018 |
| 2016/0345808 A1* | 12/2016 | Inomata | .......... | A61B 1/00181 |
| 2016/0374542 A1* | 12/2016 | Honda | ............... | A61B 1/0002 |
| | | | | 600/170 |
| 2017/0000314 A1* | 1/2017 | Honda | ............ | A61B 1/00183 |
| 2017/0014017 A1* | 1/2017 | Obara | ............ | G02B 23/2484 |
| 2017/0105608 A1* | 4/2017 | Kura | ................ | G02B 23/2423 |

FOREIGN PATENT DOCUMENTS

| | | |
|---|---|---|
| JP | 2011-120863 A | 6/2011 |
| JP | 2014-132964 A | 7/2014 |
| JP | 5583873 | 9/2014 |

\* cited by examiner

ND OSCOPE HAVING OBSERVATION
WINDOW WITH CIRCUMFERENTIAL SIDE
SURFACE AND CLEANING NOZZLES
DIRECTED TO CIRCUMFERENTIAL SIDE
SURFACE

CROSS REFERENCE TO RELATED
APPLICATION

This application is a continuation application of PCT/JP2016/083058 filed on Nov. 8, 2016 and claims benefit of Japanese Application No. 2016-006995 filed in Japan on Jan. 18, 2016, the entire contents of which are incorporated herein by this reference.

BACKGROUND OF THE INVENTION

1. Field of the Invention

The present invention relates to an endoscope, and in particular, to an endoscope that includes an observation window including a circumferential side surface formed in a cone shape.

2. Description of the Related Art

An endoscope is traditionally widely used in a medical field and an industrial field. The endoscope includes an elongated insertion section, and an observation window is provided at a distal end portion of the insertion section. Light entering through the observation window is photoelectrically converted to generate an endoscope image that is a subject image, and the endoscope image is displayed on a display apparatus.

Further, in recent years, an endoscope that allows for observation of a subject with wide visual field in order to prevent oversight of a lesion and the like also has been developed. For example, a wide-angle endoscope that has two or more visual fields for front view image, a side view image, and the like has been developed.

A foreign matter may be attached to a surface of the observation window because the endoscope is inserted into an inspection target. In a case of a medical endoscope, dirt or the like remaining in a body is attached to the observation window. Therefore, to remove the foreign matter attached to the surface of the observation window, a cleaning nozzle that ejects gas and/or liquid to clean the observation window is provided near the observation window.

For example, Japanese Patent No. 5583873 specification discloses a wide-angle endoscope that includes a front observation window for observation of a region in front of the insertion section and a side observation window for observation of a side region around the side observation window. The side observation window includes a truncated conical lens. Also in the endoscope according to the disclosure, the cleaning nozzles cleaning the front observation window and the side observation window are provided near the respective observation windows.

In particular, two cleaning nozzles that clean the side observation window of a truncated conical lens unit that has a circumferential side surface formed in a cone shape, are provided at a distal end portion of the insertion section so as to eject cleaning solution to the circular arc-shaped circumferential side surface of the side observation window from a direction orthogonal to a center axis of the truncated conical lens unit.

SUMMARY OF THE INVENTION

An endoscope according to an aspect of the present invention includes: an elongated insertion section; a first observation window that includes a tapered part on a side circumference intersecting in a longitudinal axis direction of the insertion section, and includes a circumferential side surface formed in a cone shape; and a cleaning nozzle that includes an opening part through which liquid cleaning the circumferential side surface is ejected, the opening part being inclined to direct an ejection direction of the liquid toward a distal end of the tapered part. A center position of the opening part of the cleaning nozzle is provided on proximal end side with respect to a center position of the first observation window in the longitudinal axis direction. A region that is defined by a width of the opening part and two virtual lines is provided to include a space between one end of a sector shape and both of an upper side portion and a lower side portion of the sector shape in a development diagram of the cone shape. The two virtual lines are extended parallel in the ejection direction from respective ends of the width.

An endoscope according to an aspect of the present invention includes: an elongated insertion section; an observation window that includes a tapered part on a side circumference intersecting in a longitudinal axis direction of the insertion section, and includes a circumferential side surface formed in a cone shape; a pedestal portion that is provided, adjacently to the observation window, to project from a distal end part of the insertion section in the longitudinal axis direction, and includes a side surface facing in a direction intersecting the longitudinal axis direction; and a cleaning nozzle that is provided on the pedestal portion and includes an opening part through which liquid cleaning the circumferential side surface is ejected, the opening part being inclined to direct an ejection direction of the liquid toward a distal end of the tapered part. The opening part through which the liquid cleaning the circumferential side surface is ejected is provided in the cleaning nozzle such that, when the cleaning nozzle is viewed from a direction orthogonal to the side surface of the pedestal portion, the opening part is inclined to direct the ejection direction of the liquid toward the distal end of the tapered part with respect to a plane orthogonal to a center axis of the observation window.

BRIEF DESCRIPTION OF THE DRAWINGS

FIG. 7 is a perspective view of the distal end portion 7 of the insertion section 4 of the endoscope 1 that includes a cleaning nozzle disposed in the conventional layout, to explain a reachable range of liquid ejected from an opening part 33a of the cleaning nozzle 28a;

FIG. 11 is a perspective view of the distal end portion 7 of the insertion section 4 of the endoscope 1 including the cleaning nozzle disposed in the layout of the present embodiment, to explain a reachable range of the liquid ejected from the opening part 33a of the cleaning nozzle 28a.

DETAILED DESCRIPTION OF THE PREFERRED EMBODIMENT

An embodiment of the present invention is described below with reference to drawings.
(Configuration)

Figure 1:
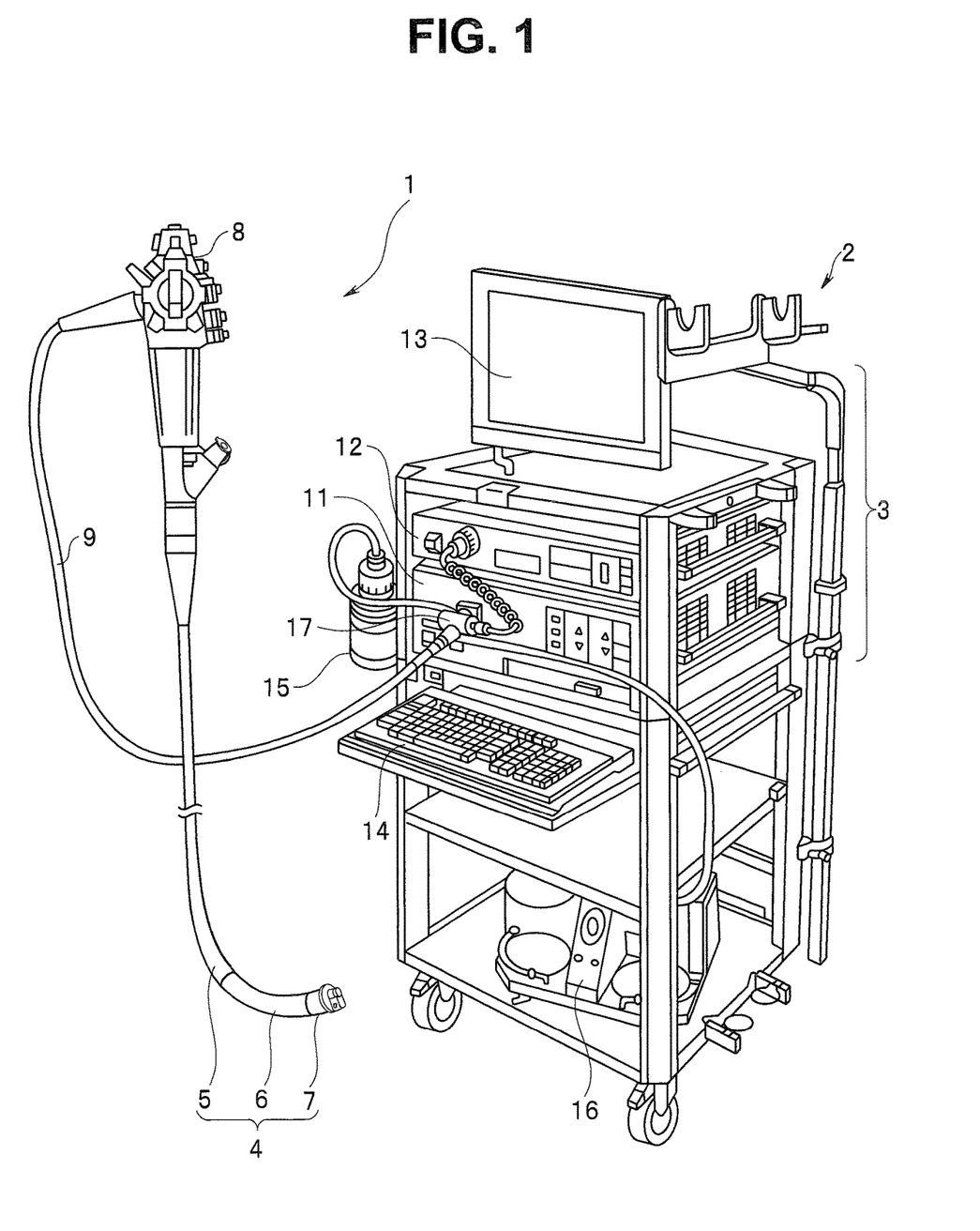
FIG. 1 is a diagram illustrating an appearance configuration of an endoscope apparatus that includes an endoscope including a front observation window and a side observation window at a distal end portion of an insertion section, and a cleaning mechanism cleaning the front observation window and the side observation window, according to an embodiment of the present invention.

FIG. 1 is a diagram illustrating an appearance configuration of an endoscope apparatus that includes an endoscope and a cleaning mechanism according to the embodiment of the present invention. The endoscope includes a front observation window and a side observation window at a distal end portion of an insertion section. The cleaning mechanism cleanes the front observation window and the side observation window.

The endoscope apparatus according to the present embodiment mainly includes an endoscope 1 and an endoscope apparatus 3 that is mounted on a movable trolley 2. In the following description, a flexible endoscope is described as an example; however, the present embodiment is similarly applicable to a rigid endoscope.

The endoscope 1 includes an elongated insertion section 4 that is inserted into a body of an observation target. The insertion section 4 includes an elongated flexible tube 5, a bending portion 6, and a distal end portion 7. The flexible tube 5 is provided on proximal end side. The bending portion 6 is provided on distal end side of the flexible tube 5. The distal end portion 7 is provided on distal end side of the bending portion 6. The endoscope 1 further includes two bending operation knobs for vertical and lateral directions, an operation section 8, and a universal cable 9. The two bending operation knobs bendably operate the bending portion 6 in the vertical and lateral directions. The operation section 8 includes various kinds of buttons such as a release button. The universal cable 9 is extended from the operation section 8.

The endoscope apparatus 3 includes a light source apparatus 11, a video processor 12, a monitor 13, a keyboard 14, and the like. The light source apparatus 11 generates illumination light applied to an observation target site. The video processor 12 performs predetermined image processing on a picked-up video signal. The monitor 13 displays the video signal as an observation image. The keyboard 14 is an input section through which a user inputs various kinds of commands and data.

Further, a bottle 15 is detachably attached to a strut of the trolley 2. The bottle 15 reserves cleaning solution that is liquid used in cleaning or the like, such as water and saline. Moreover, an air feeding pump unit (not illustrated) is disposed inside any of units of the endoscope apparatus 3. The cleaning solution is supplied to each of cleaning nozzles through unillustrated liquid feeding channels when the air from the air feeding pump unit is supplied to the bottle 15. Further, a suction unit 16 that sucks, inside the body, liquid and gas ejected from a cleaning nozzle described later into the body, is provided on a rack of the trolley 2.

The universal cable 9 is connected to the light source apparatus 11 through a connector 17. The universal cable 9 includes, in addition to a light guide made of optical fibers, a plurality of signal lines, and a supply path (an air feeding/liquid feeding channel) and a discharge path of gas and liquid. The plurality of signal lines transmit the video signal and the like. The supply path and the discharge path are each made of a tube. The connector 17 that is connected to the endoscope apparatus 3 side of the universal cable 9 is branched correspondingly to the signal lines, the tube, and the light guide, and is connected to respective configuration sites.

Figure 2:
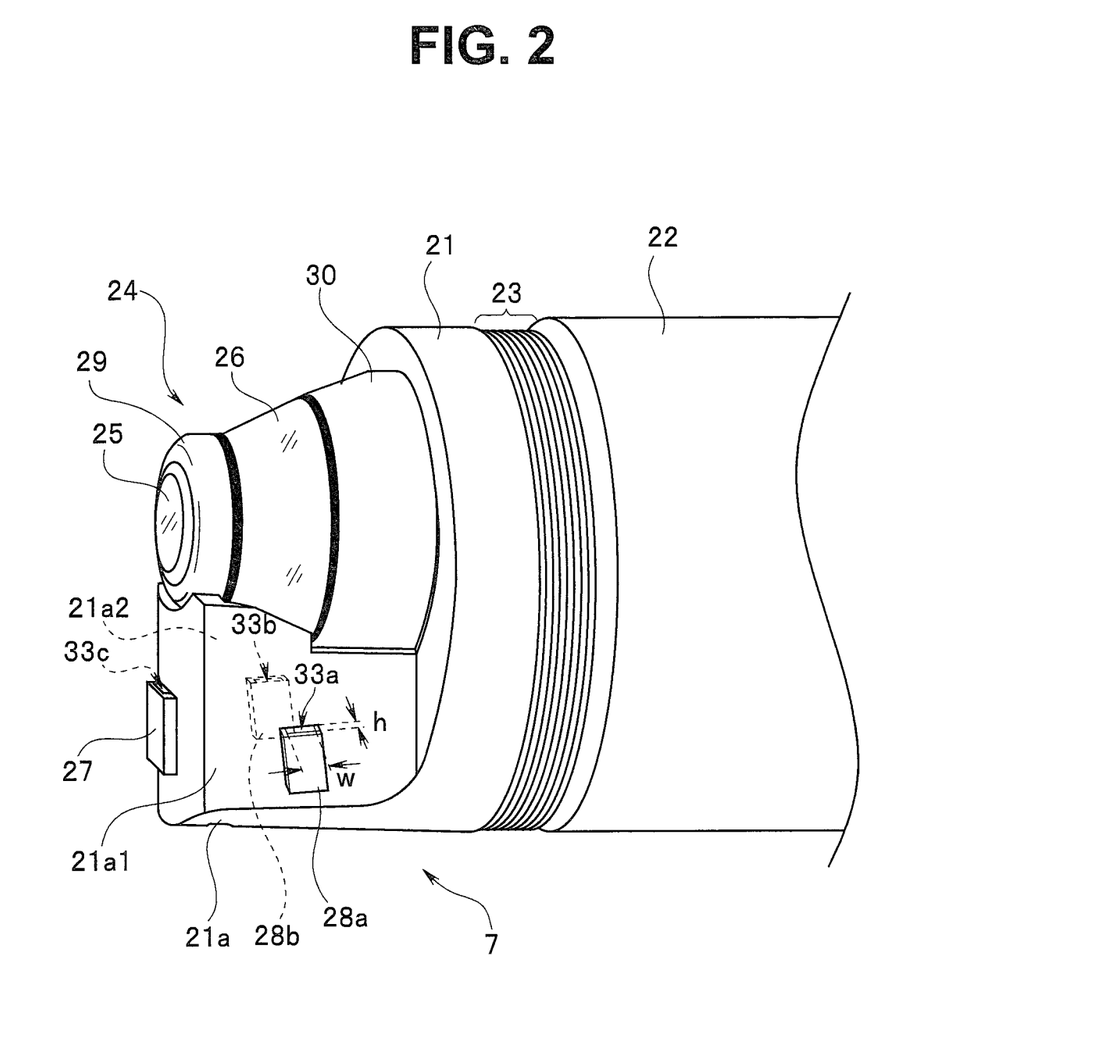
FIG. 2 is a perspective view illustrating a distal end portion 7 of an insertion section 4 of an endoscope 1 according to the embodiment of the present invention.
Figure 3:
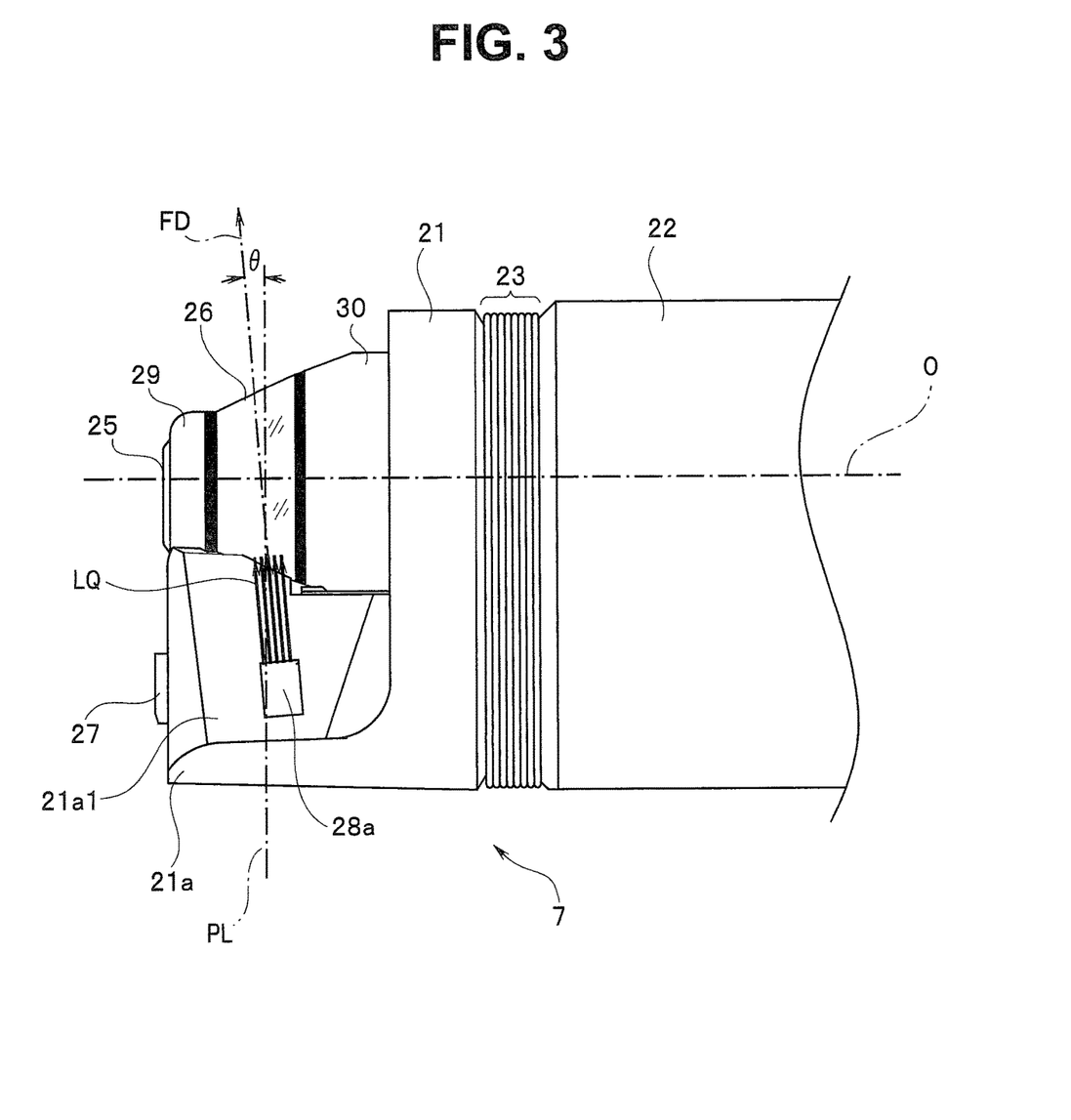
FIG. 3 is a left side view of the distal end portion 7 according to the embodiment of the present invention.

FIG. 2 is a perspective view of the distal end portion 7 of the insertion section 4 of the endoscope 1. FIG. 3 is a left side view of the distal end portion 7.

The distal end portion 7 of the insertion section 4 includes a distal end portion body 21 made of a resin. A sheath member 22 made of rubber covers the insertion section 4. A distal end portion of the sheath member 22 is fixed to the distal end portion body 21 by a spool portion 23. An adhesive is applied on the spool portion 23.

A rectangular-parallelepiped pedestal portion 21a is provided on a distal end surface of the distal end portion body 21. The pedestal portion 21a projects in a distal end direction that is an insertion direction of the insertion section 4. A lens unit 24 is provided on the distal end surface of the distal end portion body 21 so as to project adjacently to the pedestal portion 21a. The lens unit 24 has a substantially columnar shape, and includes a front observation window 25 and a side observation window 26. In other words, the pedestal portion 21a is so provided as to project from a distal end part of the insertion section 4, and the lens unit 24 is so provided adjacently to the pedestal portion 21a as to project from the distal end part of the insertion section 4.

The front observation window 25 has a circular shape and is disposed at a distal end surface of the lens unit 24. The side observation window 26 is provided in a circular arc shape along a circumferential direction on a circumferential side surface of the lens unit 24, and is disposed on rear side of the front observation window 25 (namely, proximal end side). The lens unit 24 includes an image pickup optical system of the endoscope 1, and the image pickup optical system is disposed in front of an unillustrated image pickup device. The image pickup optical system includes a plurality of lenses and lens groups for forming a picked-up image, and each of the lenses is supported by an unillustrated lens frame.

As illustrated in FIG. 2, the side observation window 26 of the lens unit 24 has a truncated cone shape. Since the side observation window 26 has the truncated cone shape, the side observation window 26 has a tapered part. In other words, the side observation window 26 is a portion of an inclined surface part of the truncated conical lens, and has a tapered shape. Therefore, the side observation window 26 has a circular arc shape including a circumferential side surface formed in a cone shape. The front observation window 25 is provided at a distal end of the side observation window 26.

In other words, the side observation window 26 has the circumferential side surface that includes the tapered part tapered from the proximal end side toward the distal end side and is formed in the cone shape, on a side circumference intersecting in the longitudinal axis direction of the insertion section 4. The front observation window 25 has an optical axis along the longitudinal axis direction at a center of the circular arc shape of the side observation window 26.

Accordingly, the front observation window 25 acquires a first subject image in a first region of a subject into which the insertion section 4 is inserted. The side observation window 26 acquires a second subject image in a second region of the subject. The second region is at least partially different from the first region. The first subject image acquired by the front observation window 25 is the subject image in the first region that includes a region in front of the insertion section 4 along the longitudinal axis direction of the insertion section 4. The second subject image acquired by the side observation window 26 is the subject image in the second region that includes a side region around the insertion section 4 in a direction intersecting the longitudinal axis direction.

The pedestal portion 21a is a distal end structure in which the distal end surface of the pedestal portion 21a has the height (projection height to the front side) substantially the same as the surface height of the front observation window 25. A cleaning nozzle 27 that cleanes the surface of the front observation window 25 is disposed on the distal end surface of the pedestal portion 21a near the front observation window 25. The cleaning nozzle 27 ejects liquid in a direction parallel to the distal end surface of the pedestal portion 21a.

Two cleaning nozzles 28a and 28b that clean the surface of the side observation window 26 are disposed on respective side surface of the pedestal portion 21a that are opposite to each other. The two cleaning nozzles 28a and 28b are provided near respective ends of the circular arc-shaped side observation window 26.

Note that an opening part (not illustrated) of a treatment instrument insertion hole that allows insertion of forceps and the like, is provided on the distal end portion body 21.

An illumination window 29 having an annular shape is so provided on the distal end part of the lens unit 24 as to surround the front observation window 25. The illumination window 29 applies the illumination light to illuminate a region in front of the distal end portion 7. Further, an illumination window 30 having a circular arc shape is provided on the proximal end side of the side observation window 26. The illumination window 30 applies illumination light to mainly illuminate a side region of the distal end portion 7, namely, a region around the distal end portion 7.

A distal end portion of the light guide (not illustrated) from which the illumination light from the light source apparatus 11 is outputted is disposed at rear side of each of the illumination windows 29 and 30.

A surface of a region between the illumination window 29 and the side observation window 26 is subjected to treatment of preventing the illumination light from the illumination window 29 from entering the side observation window 26. A surface of a region between the side observation window 26 and the illumination window 30 is also subjected to treatment of preventing the illumination light from the illumination window 30 from entering the side observation window 26.

The two cleaning nozzles 28a and 28b are provided on the pedestal portion 21a adjacent to the lens unit 24. The two cleaning nozzles 28a and 28b are respectively provided on two side surfaces 21a1 and 21a2 of the pedestal portion 21a that are parallel to each other.

More specifically, the cleaning nozzle 28a is so disposed as to project on the side surface 21a1, and ejects liquid in a direction parallel to the side surface 21a1 from one end side of the circular arc-shaped side observation window 26 that is disposed on an outer circumferential surface of the lens unit 24. The cleaning nozzle 28b is so disposed as to project on the side surface 21a2, and ejects liquid in a direction parallel to the side surface 21a2 from the other end side of the circular arc-shaped side observation window 26 that is disposed on the outer circumferential surface of the lens unit 24. The cleaning nozzles 28a and 28b respectively include opening parts 33a and 33b through which the liquid is ejected. The cleaning nozzle 27 includes an opening part 33c through which the liquid is ejected.

The cleaning nozzle 27 is provided on the distal end surface of the pedestal portion 21a such that the liquid from the opening part 33c strikes against the surface of the front observation window 25. The two cleaning nozzles 28a and 28b are provided on the respective side surfaces of the pedestal portion 21a such that the liquid from the respective opening parts 33a and 33b strikes against the surface of the side observation window 26.

Each of the opening parts 33a, 33b, and 33c is a rectangular opening that has a height h of about 0.5 mm and a width w of about 1 mm.

As illustrated in FIG. 3, the cleaning nozzle 28a is disposed such that an ejection direction FD of liquid LQ from the opening part 33a becomes a direction inclined by a predetermined angle θ from a plane PL orthogonal to a center axis O of the lens unit 24. The cleaning nozzle 28b is also disposed in a similar manner. In other words, the cleaning nozzles 28a and 28b are provided such that the ejection direction FD of the liquid LQ is inclined toward the tapered distal end side of the circumferential side surface, in order to clean the circumferential side surface of the side observation window 26.

Next, layout of the cleaning nozzles 28a and 28b is described in more detail.

Figure 4:
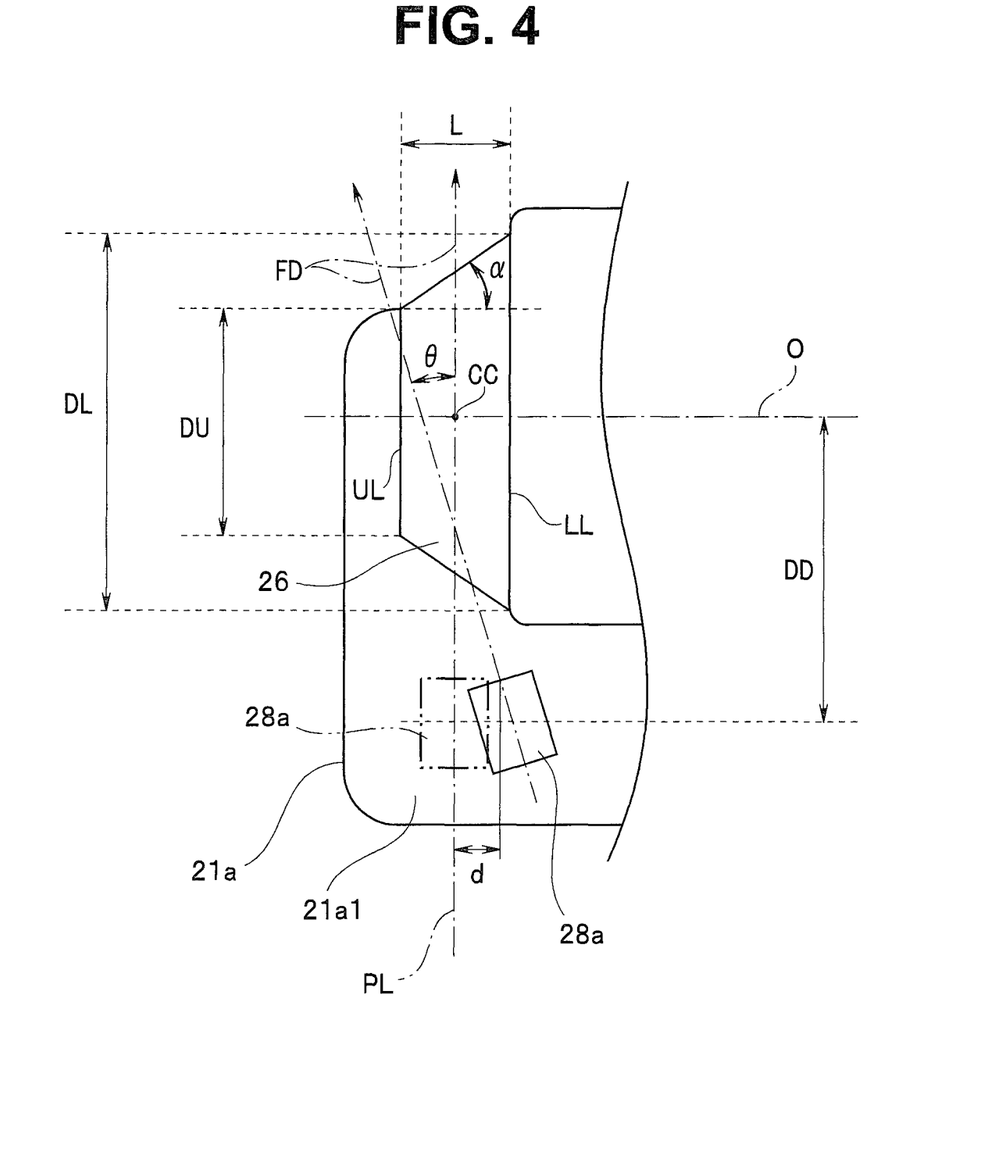
FIG. 4 is a schematic left side view of the distal end portion 7 to explain a position and inclination of a cleaning nozzle 28A with respect to a side observation window 26, according to the embodiment of the present invention.

FIG. 4 is a schematic left side view of the distal end portion 7 to explain the position and the inclination of the cleaning nozzle 28a with respect to the side observation window 26.

A diameter DU of an upper side portion UL of the truncated cone shape of the side observation window 26 is, for example, 3 mm to 5 mm, and a diameter DL of a lower side portion LL is, for example, 6 mm to 8 mm. A distance L between the upper side portion UL and the lower side portion LL, namely, a height of the circumferential side surface of the side observation window 26 in the axis direction of the lens unit 24 is about 2 mm in this case.

The upper side portion UL is located on narrow angle side of the side observation window 26, and the lower side portion LL is located on wide angle side of the side observation window 26. Therefore, the cleaning nozzles 28a and 28b are disposed such that the ejection direction FD of the liquid LQ is inclined toward the narrow angle side.

As illustrated in FIG. 4, when the distal end portion 7 is viewed from the direction orthogonal to the plane of the side surface 21a1, a distance DD between the center of each of the cleaning nozzles 28a and 28b and a center axis of the truncated cone (that is coincident with the center axis O of the lens unit 24 in FIG. 3 and FIG. 4) is, for example, 6 mm to 8 mm.

As described above, the cleaning nozzles 28a and 28b are respectively provided on the two side surfaces 21a1 and 21a2 of the pedestal portion 21a that are parallel to each other.

As illustrated in FIG. 4, when the distal end portion 7 is viewed from the direction orthogonal to the plane of the side surface 21a1, the cleaning nozzles 28a and 28b are each inclined by an angle θ from the plane PL that is parallel to the surface orthogonal to the center axis of the truncated cone (that is coincident with the center axis O of the lens unit 24 in FIG. 3 and FIG. 4).

Further, when the distal end portion 7 is viewed from the direction orthogonal to the plane of the side surface 21a1, the center of each of the opening parts 33a and 33b of the cleaning nozzles 28a and 28b (in this case, the center of each of the opening parts 33a and 33b in the width direction) is disposed at a position apart by a distance d in a proximal end direction from the plane PL that passes through a center (a center of the distance L) between the upper side portion UL and the lower side portion LL of the truncated cone shape of the side observation window 26.

In other words, the center position of each of the opening parts 33a and 33b of the respective cleaning nozzles 28a and 28b is provided on the proximal end side with respect to the center position of the side observation window 26 in the longitudinal axis direction.

In FIG. 4, a solid line indicates an installation position of the cleaning nozzle 28b, the center of the opening part 33a of which is separated from the plane PL by the distance d in the proximal end direction, and an alternate long and two short dashes line indicates a conventional installation position of the cleaning nozzle 28a.

(Action)

Next, a cleaning action of the side observation window 26 of the endoscope 1 by the above-described cleaning nozzles 28a and 28b is described.

First, a path of the liquid ejected from the cleaning nozzle disposed in conventional layout is described.

Figure 5:
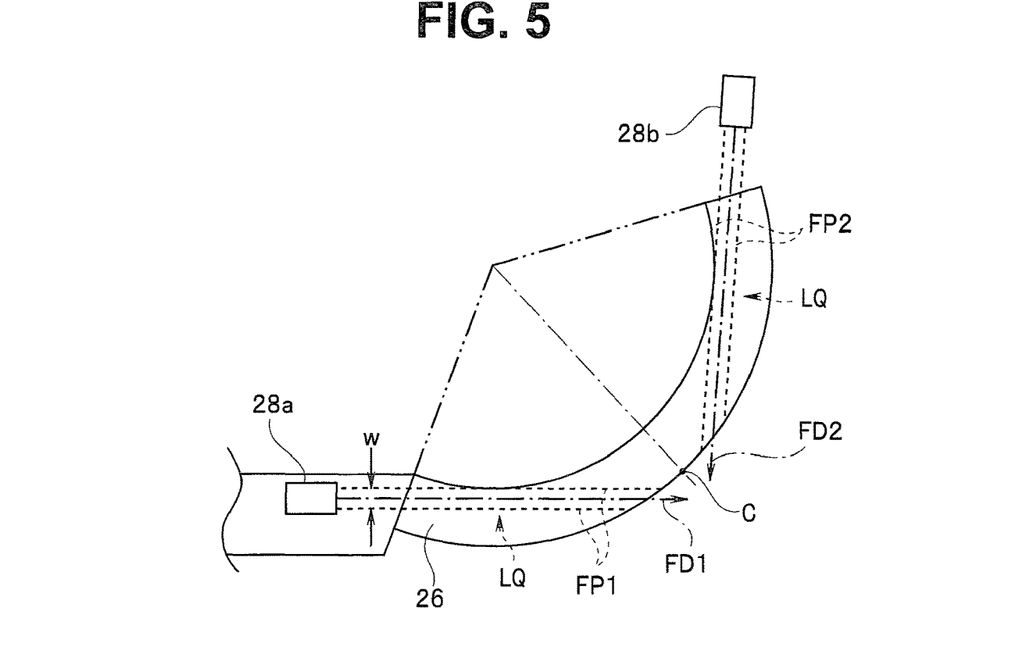
FIG. 5 is a diagram to explain a traveling direction of liquid in a case of cleaning nozzles 28a and 28b disposed in conventional layout illustrated by an alternate long and two short dashes line in FIG. 4.

FIG. 5 is a diagram to explain the traveling direction of the liquid in the case of the cleaning nozzles 28a and 28b disposed in the conventional layout illustrated by the alternate long and two short dashes line in FIG. 4. FIG. 5 illustrates a state in which the circumferential side surface of the side observation window 26 having the truncated cone shape is developed on a plane, and the developed side observation window 26 has a sector shape.

As illustrated by the alternate long and two short dashes line in FIG. 4, the cleaning nozzle 28a is disposed on the side surface 21a1 such that the ejection direction FD of the liquid LQ becomes parallel to the upper side portion UL and the lower side portion LL. Likewise, the cleaning nozzle 28b is also disposed on the side surface 21a2 such that the ejection direction FD of the liquid LQ becomes parallel to the upper side portion UL and the lower side portion LL.

In the case of the conventional layout, as illustrated in FIG. 5, the liquid ejected from the cleaning nozzle 28a travels along an ejection direction FD1 while having the width w of the opening part 33a illustrated by dashed lines. Likewise, the liquid ejected from the cleaning nozzle 28b also travels along an ejection direction FD2 while having the width w of the opening part 33b illustrated by dashed lines.

The liquid LQ ejected from the opening parts 33a and 33b of the respective cleaning nozzles 28a and 28b actually travels on the side surfaces 21a1 and 21a2 while having a width larger than the width w due to contact resistance with the side surfaces 21a1 and 21a2. When the liquid LQ strikes against the side observation window 26, the liquid LQ travels on the surface of the side observation window 26 while further spreading due to contact resistance with the surface of the side observation window 26.

The liquid LQ ejected from the cleaning nozzles 28a and 28b straightly travels respectively along the ejection directions FD1 and FD2; however, the liquid LQ is difficult to reach a center C of the lower side portion LL that is far from the end of the side observation window 26, as illustrated in FIG. 5. In the case of FIG. 5, the liquid LQ ejected from the opening parts 33a and 33b respectively travels on the side surfaces 21a1 and 21a2, and then travels on the surface of the side observation window 26 having the truncated cone shape; however, the liquid LQ is difficult to reach the center C of the lower side portion LL of the side observation window 26.

The distal end portion 7 of the insertion section 4 takes various postures inside the body during endoscopy. Therefore, the distal end portion 7 is used in various directions such as an up direction, a down direction, and an inclined direction, with respect to a horizontal direction. In addition, during the endoscopy, the distal end portion 7 rotates around the axis of the insertion section 4. Therefore, the cleaning nozzles 28a and 28b may be located at upper side portion, at lower side portion, or in the inclined direction, with respect to the side observation window 26 of the lens unit 24, in the gravity direction.

Accordingly, in the case of the cleaning nozzle 28a disposed in the conventional layout, in cleaning of the side observation window 26, the liquid LQ may spread over the entire surface of the side observation window 26 in some cases; however, cleanability of the side observation window 26 is not high because in the ejection directions FD1 and FD2, it is difficult for the liquid LQ to reach the center C of the circular arc-shaped lower side portion LL of the side observation window 26 as illustrated in FIG. 5.

Next, ejection of the liquid by the cleaning nozzle disposed in layout of the present embodiment is described.

Figure 6:
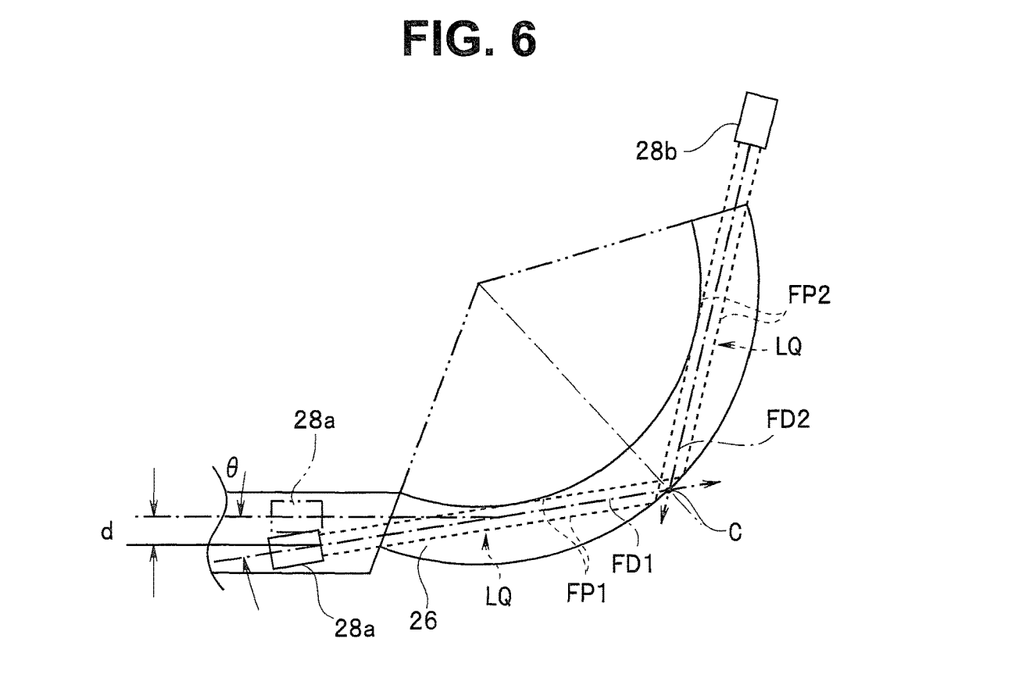
FIG. 6 is a diagram to explain an ejection direction of liquid in a case of the cleaning nozzle 28a disposed in layout of the present embodiment illustrated by a solid line in FIG. 4.

FIG. 6 is a diagram to explain the ejection direction of the liquid in the case of the cleaning nozzle 28a disposed in the layout of the present embodiment illustrated by the solid line in FIG. 4. FIG. 6 illustrates a state in which the circumferential side surface of the side observation window 26 having the truncated cone shape is developed on a plane.

As illustrated by the solid line in FIG. 4, the cleaning nozzle 28a is disposed on the side surface 21a1 such that the ejection direction FD of the liquid LQ is inclined toward the upper side portion UL. Likewise, the cleaning nozzle 28b is also disposed on the side surface 21a2 such that the ejection direction FD of the liquid LQ is inclined toward the upper side portion UL. In FIG. 6, the liquid LQ from the cleaning nozzle 28a is ejected in the ejection direction FD1, and the liquid from the cleaning nozzle 28b is ejected in the ejection direction FD2.

The liquid LQ ejected from the cleaning nozzles 28a and 28b straightly travels respectively along the ejection directions FD1 and FD2, and the liquid LQ ejected from the opening parts 33a and 33b easily reaches the center C of the lower side portion LL as illustrated in FIG. 6 because the cleaning nozzles 28a and 28b are disposed such that the ejection direction FD of the liquid LQ is inclined toward the upper side portion UL. In the case of FIG. 6, the liquid LQ in the ejection directions FD1 and FD2 has reached the center C of the circular arc-shaped lower side portion LL of the side observation window 26.

In other words, the liquid LQ ejected from the opening parts 33a and 33b of the cleaning nozzles 28a and 28b easily reaches throughout the lower side portion LL of the side observation window 26. In the case of FIG. 6, the ejection directions FD1 and FD2 of the liquid reach the center C of the circular arc-shaped lower side portion LL of the side observation window 26.

Figure 7:
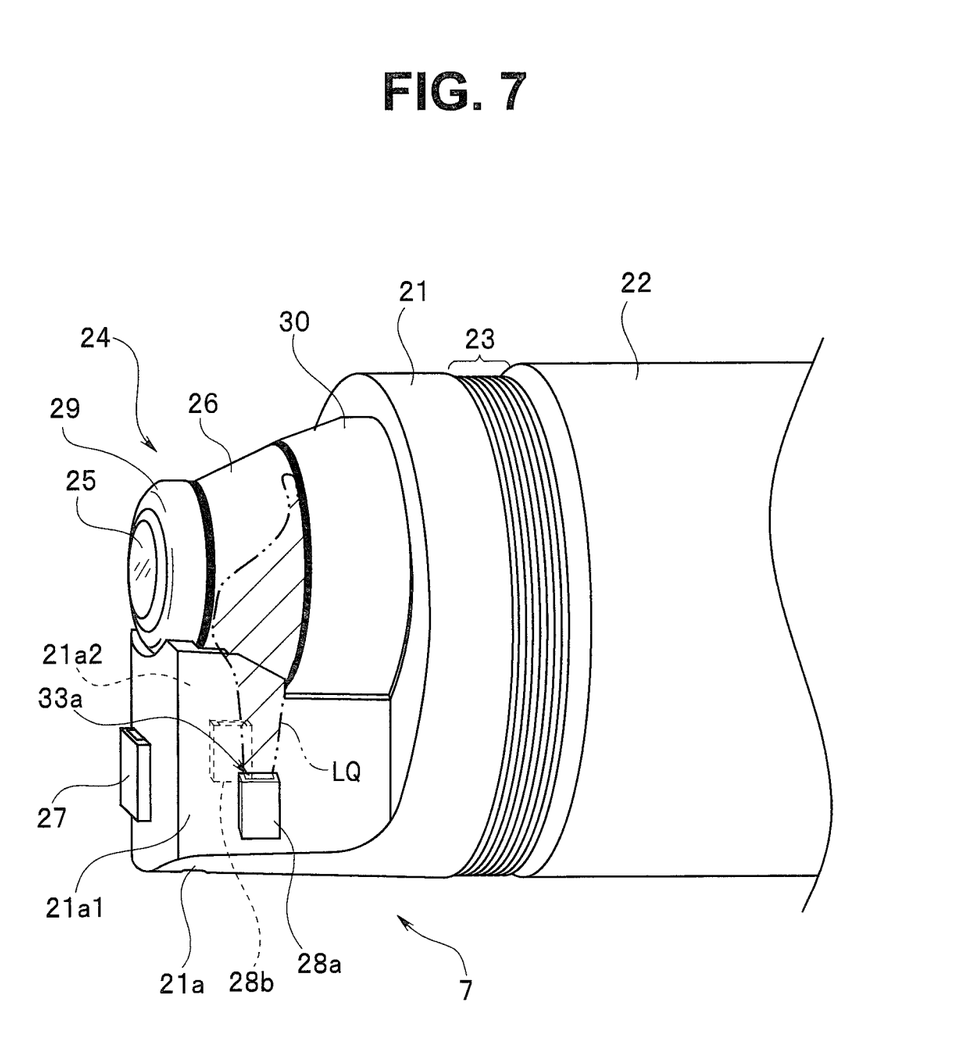

FIG. 7 is a perspective view of the distal end portion 7 of the insertion section 4 of the endoscope 1 that includes the cleaning nozzle disposed in the conventional layout, to explain a reachable range of the liquid ejected from the opening part 33a of the cleaning nozzle 28a. In FIG. 7, the reachable range of the liquid LQ ejected from the cleaning nozzle 28a is illustrated by hatching.

As described above, the distal end portion 7 of the insertion section 4 is used in various directions such as the up direction, the down direction, and the inclined direction with respect to the horizontal direction, and rotates around the axis of the insertion section 4, during the endoscopy. Accordingly, in the case of the cleaning nozzle 28a disposed in the conventional layout, the liquid may spread over the entire surface of the side observation window 26 in cleaning in some cases. As illustrated in FIG. 5, however, since the ejection directions FD1 and FD2 of the liquid do not reach the center C of the circular arc-shaped lower side portion LL of the side observation window 26, the liquid may be difficult to spread over the entire surface of the side observation window 26 in some cases.

Figure 8:
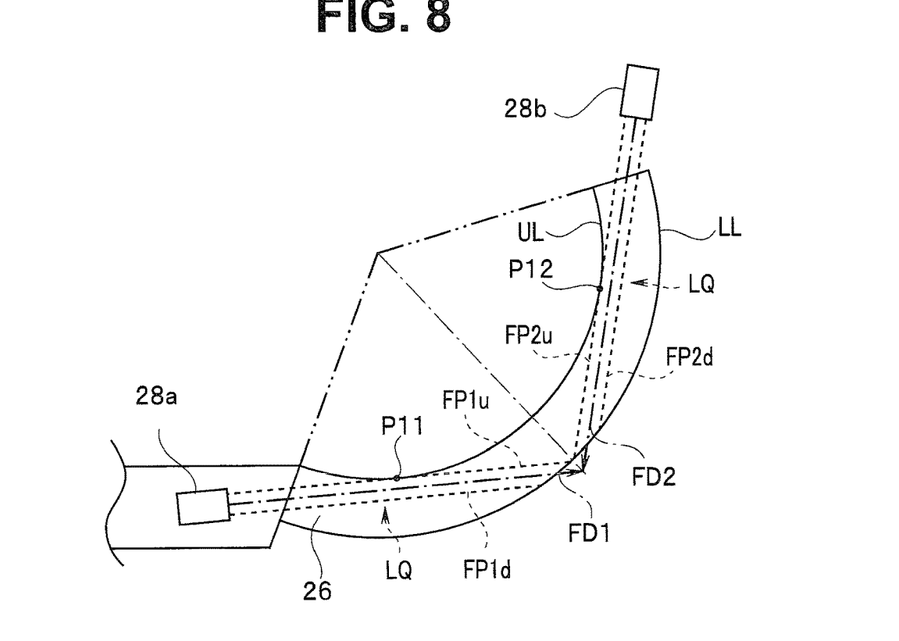
FIG. 8 is a diagram to explain the position of the cleaning nozzle 28a when ejection directions FD1 and FD2 of liquid LQ ejected from respective opening parts 33a and 33b are inclined toward a tapered distal end of a lens unit 24, according to the embodiment of the present invention.
Figure 9:
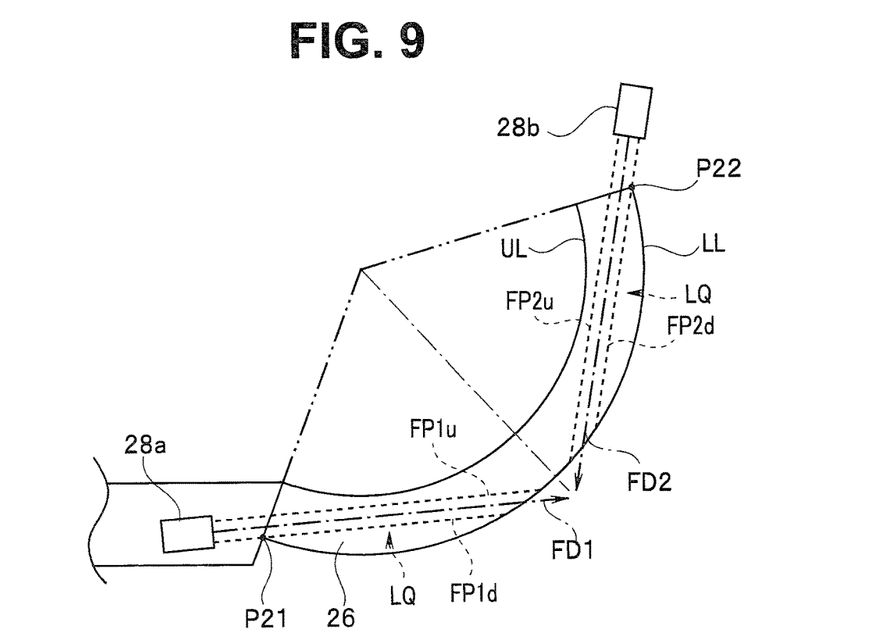
FIG. 9 is a diagram to explain the position of the cleaning nozzle 28a when the ejection directions FD1 and FD2 of the liquid LQ ejected from the respective opening parts 33a and 33b are inclined toward the tapered distal end of the lens unit 24, according to the embodiment of the present invention.

FIG. 8 and FIG. 9 are diagrams to explain the position of the cleaning nozzle 28a when the ejection directions FD1 and FD2 of the liquid LQ respectively ejected from the opening parts 33a and 33b are inclined toward the tapered distal end of the lens unit 24.

The liquid LQ ejected from the opening parts 33a and 33b travels while spreading on the side surfaces 21a1 and 21a2 and on the surface of the side observation window 26. As illustrated in FIG. 8 and FIG. 9, however, the liquid LQ energetically travels within a region defined by extension lines FP1 and FP2 from both ends of the opening parts 33a and 33b along the ejection directions FD1 and FD2 of the liquid LQ.

The cleaning nozzle 28a is disposed to cause the ejection direction of the liquid LQ to be inclined toward the upper side portion UL such that the region, namely, the range defined by extension lines FP1u and FP1d from the opening part 33a is located between the upper side portion UL and the lower side portion LL of the side observation window 26. Likewise, the cleaning nozzle 28b is disposed to cause the ejection direction of the liquid LQ to be inclined toward the upper side portion UL such that the region, namely, the range defined by extension lines FP2u and FP2d from the opening part 33b is located between the upper side portion UL and the lower side portion LL of the side observation window 26.

In other words, the cleaning nozzles 28a and 28b are provided such that the region defined by the width w of the opening part 33a and the extension lines FP1u and FP1d that are two virtual lines extending parallel in the ejection direction FD1 from both ends of the width, and the region defined by the width w of the opening part 33b and the extension lines FP2u and FP2d that are two virtual lines extending parallel in the ejection direction FD2 from both ends of the width are located between both ends of the sector shape and both of the upper side portion UL and the lower side portion LL of the sector shape in the development diagram of the cone shape.

In FIG. 8, the extension line FP1u of the cleaning nozzle 28a is a tangent line with the upper side portion UL and is in contact with the upper side portion UL at a point P11. In FIG. 8, the extension line FP2u of the cleaning nozzle 28b is also a tangent line with the upper side portion UL and is in contact with the upper side portion UL at a point P12.

In FIG. 9, the extension line FP1d of the cleaning nozzle 28a is a tangent line with the lower side portion LL, and is in contact with the lower side portion LL at a point P21. In FIG. 9, the extension line FP2d of the cleaning nozzle 28b is also a tangent line with the lower side portion LL, and is in contact with the lower side portion LL at a point P22. The points P21 and P22 are end points of the lower side portion LL.

Accordingly, ranges defined by the extension lines FP1u, FP1d, FP2u, and FP2d from the opening parts 33a and 33b of the respective cleaning nozzles 28a and 28b are preferably located between the upper side portion UL and the lower side portion LL of the side observation window 26 when the cleaning nozzles 28a and 28b are disposed such that the ejection directions of the liquid LQ are inclined toward the upper side portion UL.

When a portion of the two ranges defined by the extension lines FP1u, FP1d, FP2u, and FP2d from the opening parts 33a and 33b of the respective cleaning nozzles 28a and 28b is located beyond the upper side portion UL or the lower side portion LL of the side observation window 26, the amount of the liquid flowing on the surface of the side observation window 26 is decreased.

Figure 10:
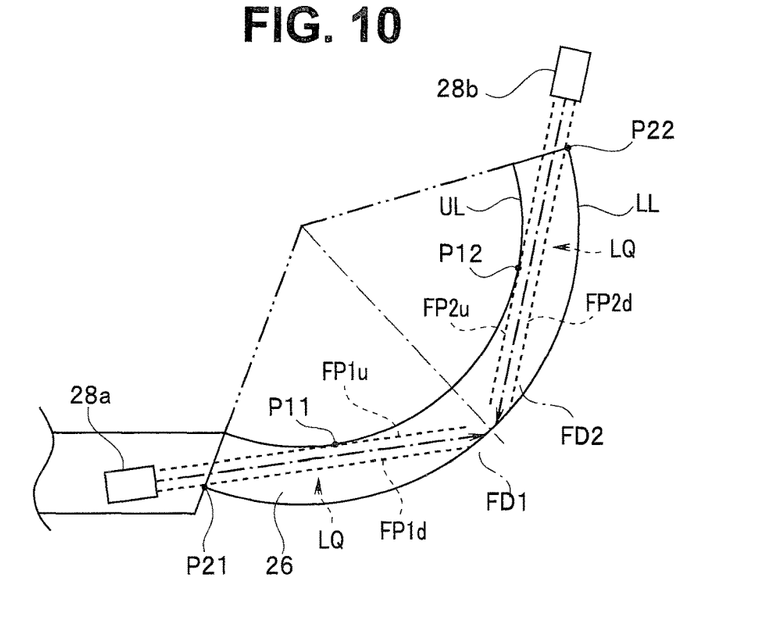
FIG. 10 is a diagram to explain another example of the position of the cleaning nozzle 28a when the ejection directions FD1 and FD2 of the liquid LQ ejected from the respective opening parts 33a and 33b are inclined toward the tapered distal end of the lens unit 24, according to the embodiment of the present invention.

FIG. 10 is a diagram to explain another example of the positions of the respective cleaning nozzles 28a and 28b when the ejection directions FD1 and FD2 of the liquid LQ ejected respectively from the opening parts 33a and 33b are inclined toward the tapered distal end of the lens unit 24.

In FIG. 10, the extension line FP1u from the cleaning nozzle 28a is in contact with the upper side portion UL at the point P11, and the extension line FP1d is in contact with the lower side portion LL at the point P21. Likewise, the extension line FP2u from the cleaning nozzle 28b is also in contact with the upper side portion UL at the point P12, and the extension line FP2d is in contact with the lower side portion LL at the point P22.

In other words, in FIG. 10, the cleaning nozzles 28a and 28b are disposed to cause the ejection directions of the liquid LQ to be inclined toward the upper side portion UL such that the ranges defined by the extension lines FP1u, FP1d, FP2u, and FP2d from the opening parts 33a and 33b of the respective cleaning nozzles 28a and 28b are located between the upper side portion UL and the lower side portion LL of the side observation window 26, and the two extension lines FP1u and FP2u come into contact with the upper side portion UL and the extension lines FP1d and FP2d come into contact with the respective end portions of the lower side portion LL.

In the case of the layout illustrated in FIG. 10, it is possible to spread the liquid LQ from the cleaning nozzles 28a and 28b over the wide range on the narrow angle side of the side observation window 26.

Figure 11:
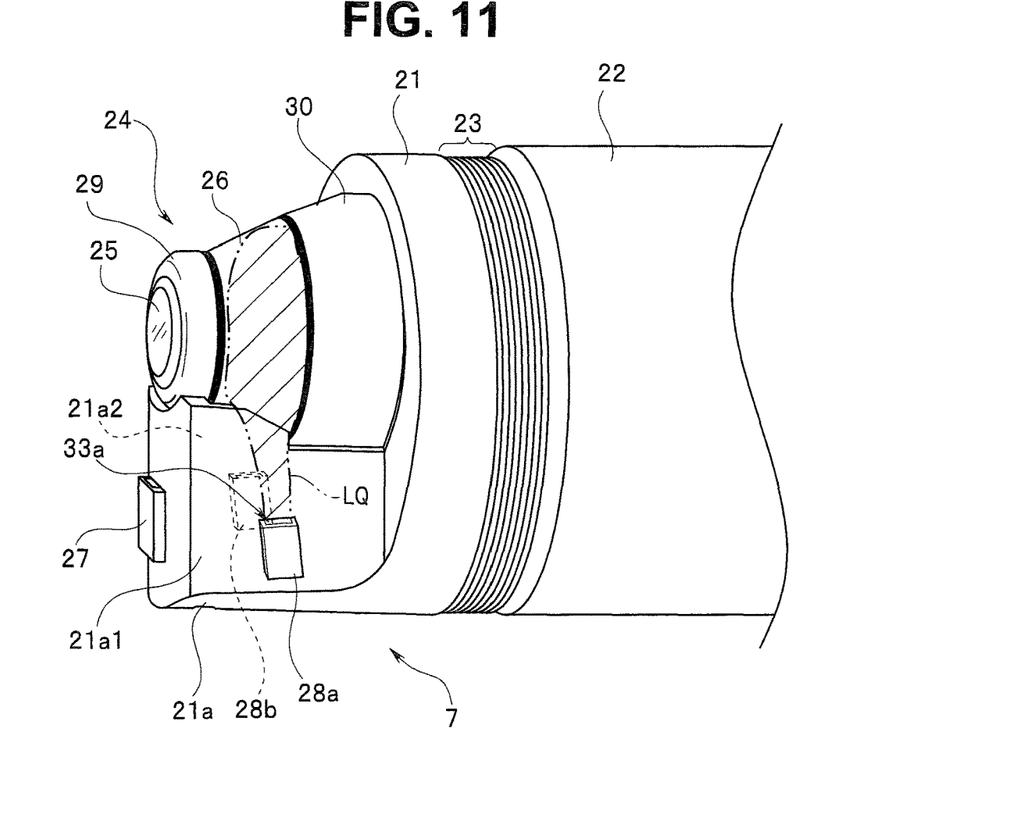

FIG. 11 is a perspective view of the distal end portion 7 of the insertion section 4 of the endoscope 1 that includes the cleaning nozzle disposed in the layout of the present embodiment, to explain the reachable range of the liquid ejected from the opening part 33a of the cleaning nozzle 28a. In FIG. 11, the reachable range of the liquid LQ ejected from the cleaning nozzle 28a is illustrated by hatching.

In a case of an inclination angle α (for example, 25 degrees) of the circumferential side surface of the side observation window 26 with respect to the center axis O of the lens unit 24 (see FIG. 4), when the center of the opening part of the cleaning nozzle is separated from the plane PL by the distance d in the proximal end direction within the range described in FIG. 8 to FIG. 10 such that the ejection directions of the liquid LQ from the cleaning nozzles 28a and 28b are inclined toward the upper side portion UL by the predetermined angle θ, the liquid LQ easily reaches the center C on the wide angle side of the side observation window 26, as illustrated in FIG. 11.

As described above, the above-described embodiment makes it possible to provide the endoscope including the cleaning nozzles that easily spread the cleaning solution to the entire circumferential surface of the observation window including the conical circumferential side surface.

The present invention is not limited to the above-described embodiment, and may be variously modified and alternated without departing from the scope of the present invention.

What is claimed is:

1. An endoscope, comprising:
an elongated insertion section;
a first observation window that includes a tapered part on a side circumference intersecting in a longitudinal axis direction of the insertion section, the first observation window including a circumferential side surface formed in a cone shape, the cone shape being formed in a circular arc shape on the circumferential side surface;
two cleaning nozzles that each include an opening through which liquid is ejected; and,
a pedestal portion projecting from a distal end part of the insertion section in the longitudinal axis direction, the pedestal portion including two side surfaces formed along the longitudinal axis direction, wherein
the two cleaning nozzles are provided on the two side surfaces, respectively,
a center of the opening of each of the two cleaning nozzles in the longitudinal axis direction is closer to a proximal end of the tapered part than to a distal end of the tapered part, and
the two cleaning nozzles are inclined distally to direct the liquid in an ejection direction toward the distal end of the tapered part to clean the circumferential side surface.

2. The endoscope according to claim 1, further comprising a second observation window that includes an optical axis along the longitudinal axis direction, at a center axis of the circular arc shape of the first observation window.

3. The endoscope according to claim 2, wherein
the second observation window acquires a first subject image in a first region of a subject into which the insertion section is inserted, and
the first observation window acquires a second subject image in a second region of the subject, the second region being at least partially different from the first region.

4. The endoscope according to claim 3, wherein
the first subject image is a subject image in the first region that includes a region in front of the insertion section along the longitudinal axis direction, and
the second subject image is a subject image in the second region that includes a side region around the insertion section in a direction intersecting the longitudinal axis direction.

5. The endoscope according to claim 1, further comprising a lens unit provided, adjacently to the pedestal portion, to project from the distal end part of the insertion section, wherein
the first observation window is provided on the lens unit.

6. The endoscope according to claim 1, wherein
the two cleaning nozzles are provided such that the liquid strikes a range from respective ends of the circular arc-shaped first observation window to a center of the first observation window.

7. The endoscope according to claim 1, wherein the cleaning nozzle is provided to be inclined distally by about four degrees toward the distal end of the tapered part.

8. The endoscope according to claim 1, wherein:
the two cleaning nozzles are inclined distally at an incline angle relative to a plane orthogonal to a longitudinal axis of the insertion section;
the opening of each of the two nozzles have a first side and a second side defining a width; and
a virtual line extending from each of the first side and the second side at the inclined angle intersects the circumferential side surface.

9. An endoscope, comprising:
an elongated insertion section;
a first observation window that includes a tapered part on a side circumference intersecting in a longitudinal axis direction of the insertion section, the first observation window including a circumferential side surface formed in a cone shape, the cone shape being formed in a circular arc shape on the circumferential side surface;
a second observation window that includes an optical axis along the longitudinal axis direction, at a center axis of the circular arc shape of the first observation window:
a pedestal portion projecting from a distal end part of the insertion section in the longitudinal axis direction, the pedestal portion including two side surface formed along the longitudinal axis direction; and
two cleaning nozzles provided on the pedestal portion, each of the two cleaning nozzles including an opening through which liquid is ejected, wherein
the two cleaning nozzles are provided on the two side surfaces, respectively, and
when the two cleaning nozzles are viewed from a direction orthogonal to the side surfaces of the pedestal portion, the two cleaning nozzles are inclined distally to direct the liquid in an ejection direction toward a distal end of the tapered part to clean the circumferential side surface.

10. The endoscope according to claim 9, wherein:
the two cleaning nozzles are inclined distally at an incline angle relative to a plane orthogonal to a longitudinal axis of the insertion section;
the opening of each of the two nozzles have a first side and a second side defining a width; and a virtual line extending from each of the first side and the second side at the inclined angle intersects the circumferential side surface.

\* \* \* \* \*